United States Patent
Spehr et al.

(10) Patent No.: US 6,650,921 B2
(45) Date of Patent: Nov. 18, 2003

(54) CARDIAC LEAD WITH MINIMIZED INSIDE DIAMETER OF SLEEVE

(75) Inventors: Paul R. Spehr, Lake Jackson, TX (US); Elmar R. Fischer, Sr., Lake Jackson, TX (US); James E. Machek, Lake Jackson, TX (US)

(73) Assignee: Intermedics Inc., Angleton, TX (US)

( * ) Notice: Subject to any disclaimer, the term of this patent is extended or adjusted under 35 U.S.C. 154(b) by 0 days.

(21) Appl. No.: 09/994,389

(22) Filed: Nov. 26, 2001

(65) Prior Publication Data

US 2002/0035319 A1 Mar. 21, 2002

Related U.S. Application Data

(62) Division of application No. 08/902,687, filed on Jul. 30, 1997, now Pat. No. 6,324,415.

(51) Int. Cl.[7] ............................................. A61B 5/04
(52) U.S. Cl. .................. 600/374; 600/375; 607/119; 607/122; 607/126
(58) Field of Search ....................... 607/101–102, 607/122, 126, 127, 129, 119, 116, 128; 600/372–377

(56) References Cited

U.S. PATENT DOCUMENTS

| 4,351,345 A | 9/1982 | Carney ...................... 128/786 |
| 4,567,901 A | 2/1986 | Harris ........................ 128/786 |
| 4,608,986 A | 9/1986 | Beranek et al. ............. 128/786 |
| 5,122,115 A | 6/1992 | Marks ........................... 604/53 |
| 5,129,404 A | 7/1992 | Spehr et al. ................ 128/785 |
| 5,246,014 A | 9/1993 | Williams et al. ............ 607/122 |
| 5,324,321 A | 6/1994 | Pohndorf et al. ........... 607/116 |
| 5,358,517 A | 10/1994 | Pohndorf et al. ........... 607/116 |
| 5,480,420 A | 1/1996 | Hoegnelid et al. .......... 607/116 |
| 5,524,337 A | 6/1996 | Houser et al. ................ 29/825 |
| 5,769,077 A | 6/1998 | Lindegren ................... 128/642 |
| 5,851,227 A | 12/1998 | Spehr ......................... 607/126 |
| 5,935,159 A * | 8/1999 | Cross et al. ................ 607/116 |
| 6,119,042 A | 9/2000 | Verness et al. ............. 607/122 |

FOREIGN PATENT DOCUMENTS

WO 95/13844 6/1995 ............ A61N/1/05

OTHER PUBLICATIONS

"Temporary Transcutaneous Pacing Wire Extension Lead Model 366–02", Sales Brochure Published by Intermedics, Inc., (1982).

* cited by examiner

Primary Examiner—Linda C. M. Dvorak
Assistant Examiner—David M Ruddy
(74) Attorney, Agent, or Firm—Schwegman, Lundberg, Woessner & Kluth, P.A.

(57) ABSTRACT

A lead assembly adapted for endocardial fixation to a human heart is provided. The lead assembly includes a lead body that has a proximal end provided with a connector for electrical connection to a cardiac stimulator. The cardiac stimulator may be a pacemaker, a cardioverter/defibrillator, or a sensing instrument. The distal end of the lead body is connected to a tubular electrode housing. The lead body consists of one or more noncoiled conductor cables surrounded by a coextensive insulating sleeve. Each conductor cable consists of a conducting element covered by a coextensive insulating sleeve. The conducting element may be a single filament wire or a plurality of individual conductor wires. In contrast to conventional leads, the lead body of the present invention does not require coiled conductor wires. Lead body diameters of 1.04 mm or smaller are possible.

19 Claims, 7 Drawing Sheets

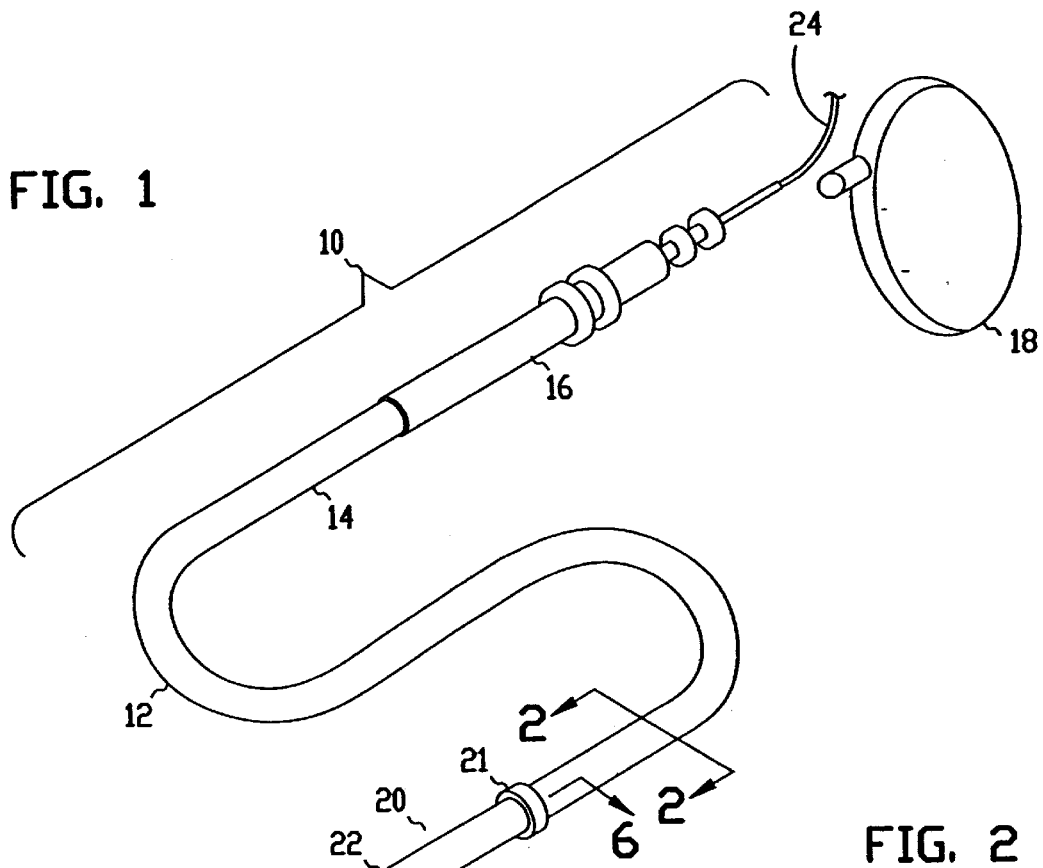
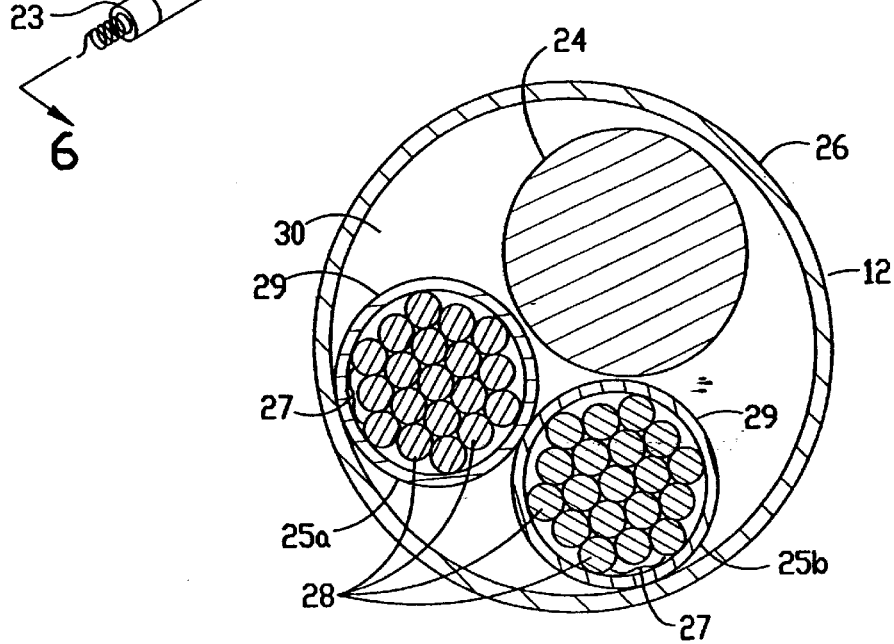

CARDIAC LEAD WITH MINIMIZED INSIDE DIAMETER OF SLEEVE

CROSS-REFERENCE TO RELATED APPLICATION(S)

This application is a division of U.S. patent application Ser. No. 08/902,687, filed on Jul. 30, 1997, now U.S. Pat. No. 6,324,415, the specification of which is hereby incorporated by reference.

FIELD OF THE INVENTION

This invention relates generally to cardiac stimulation leads, and more particularly to an implantable cardiac stimulation lead which employs a lead body encasing a very thin noncoiled conductor cable.

DESCRIPTION OF THE RELATED ART

Prior to the advent of implantable endocardial stimulation leads, surgeons and cardiologists possessed few options for providing permanent or semi-permanent electrophysiological therapy to patients suffering from cardiac arrhythmia. In cases where drug therapy and corrective surgery were ruled out, epicardial leads used with external, and later implantable, pulse generators represented the normal clinical approach. For many patients whose arrhythmia stemmed from disruptions in electrical signal propagation at highly localized spots deep within the heart, epicardial stimulation constituted a compromise treatment.

The introduction of endocardial leads capable of transvenous implantation created a boon for many cardiac arrhythmia patients. Many individuals who formerly faced the prospects of median sternotomy or thoracotomy and reliance on epicardial stimulation for endocardially originated malfunctions could be provided with a subcutaneously implanted cardiac stimulator combined with a transvenous lead that promised to yield better cosmetic results as well as the potential for better therapy through more accurate placement of lead electrodes.

Despite the myriad of advantages associated with endocardial leads, there has always been a tradeoff associated with their usage in many patients. On the one hand, transvenous implantable leads typically yield better cosmetic results and the potential for more accurate arrhythmia therapy for patients. On the other, like any foreign body introduced into the cardiovascular system, a transvenous cardiac lead presents an obstruction to the normal flow of blood, and possibly the normal operation of one or more of the valves of the heart. This partial occlusion of a portion of the patient's cardiovascular system may result in not only a diminished blood flow, but also may lead to the formation of microemboli.

For the majority of patients, the medical advantages associated with endocardial leads strongly outweigh the attendant obstruction to normal blood flow. However, for some patients, the calculation is less clear. Pediatric patients often present blood vessels that are simply too small to accommodate conventional implantable leads, and these young patients are often the least able to adjust successfully to a diminished blood flow and/or valve function. Similarly, those patients who present occluded vessels and/or eroded valve leaves resulting from disease, injury, or some other mechanism may not be suitable candidates for transvenous implanted leads. In these types of cases, epicardial leads may present the only viable solution for the arrhythmia patient.

The magnitude of blood flow area of a given vessel obstructed by a conventional endocardial lead is a function of the diameter of the lead body. Early designs for endocardial leads consisted of an elongated lead body that included a proximal connector for connection to a pulse generator and a distally located electrode for transmitting signals to the heart. The lead body consisted of a tubular insulating sleeve that jacketed a coiled conductor wire leading from the electrode to the connector. The conductor wire was coiled in a helical fashion to leave a centrally disposed lumen through which a stylet could be inserted to manipulate the lead. The minimum overall diameter for this design is limited by the sum of the diameter of the lumen, twice the diameter of the conductor wire, and twice the wall thickness of the sleeve. An early bipolar variant incorporated two coiled conductor wires separately disposed in respective lumens. Here, the minimum diameter is a function of the sum of the diameters of both lumens, twice the diameter of the conductor wire, and twice the thickness of the sleeve. Diameters of 8 French (approximately 2.7 mm) (1 French=3×diameter in millimeters)) were not uncommon.

Later lead designs incorporated a coaxial arrangement that represented an advance in miniaturization. The coaxial lead utilizes a lead body with an inner conductor wire defining a lumen, an outer conductor wire, an intermediary insulating sleeve separating the two conductor wires, and an outer insulating sleeve. The minimum diameter of the coaxial bipolar lead body is limited by the sum of the diameters of the lumen, the first conductor coil, the intermediary insulator sleeve, the second conductor coil, and the outer sleeve. Overall diameters of about 6 French (approximately 2 mm) are common with this design.

A recent improvement upon the coaxial bipolar design incorporates nested and individually insulated conductor wires that circumscribe a concentrically located lumen. This uniaxial design can be seen in the Thinline™ (a trademark of Sulzer Intermedics, Inc.) leads produced by Sulzer Intermedics, Inc. The diameter of the Thinline™ lead body is a function of the sum of the diameter of the lumen, the diameter of each of the conductor wires, and twice the wall thickness of the outer sleeve. The introduction of the Thinline™ lead design further reduced the minimum diameter of the lead body to about 4.7 French (approximately 1.6 mm).

Despite advances in miniaturization, there are still several disadvantages associated with conventional lead designs. Conventional lead bodies require an internal lumen that is coextensive with the lead body to accommodate an internal stylet for manipulating the lead. The diameter of the lumen often constitutes a significant portion of the overall diameter of the lead body and therefore represents a limitation on the achievable miniaturization of the lead body. Similarly, conventional lead bodies incorporate coiled conductor wires that, by definition, contribute twice their own diameters to the overall diameter of the lead body. For these reasons the smallest available conventional leads may still be too large for successful transvenous implantation in some patients.

In addition, coaxial leads are susceptible to structural failure due to a phenomenon commonly known as "subclavian crush." Subclavian crush occurs when a lead is implanted via the subclavian vein (a common transvenous entry site) and is pressed against the patient's clavicle during movement of the shoulder joint. The pressing force may bend the coils of the lead wire to fracture. The problem is exacerbated if the patient suffers an externally applied trauma in the clavicle area.

The present invention is directed to overcoming or minimizing one or more of the foregoing disadvantages.

SUMMARY OF THE INVENTION

In accordance with one aspect of the present invention, a lead assembly is provided. The lead assembly includes a tubular housing that has a proximal end, a fixation mechanism, and a first electrode. A lead body is provided that has a first end coupled to the proximal end of the tubular housing, second end, a first elongated noncoiled conductor cable that is in electrical communication with the first electrode, and an insulative sleeve coating the first noncoiled conductor cable. A connector for coupling to a cardiac stimulator is included that has a distal end coupled to the second end of the lead body.

In accordance with another aspect of the present invention, a lead assembly is provided. The lead assembly includes a connector that has a proximal end for coupling to a cardiac stimulator. A first noncoiled conductor cable is coupled to the connector and has a first distal end. A first electrode is coupled to the first distal end of the first noncoiled conductor cable. The first electrode has a fixation mechanism. An insulative sleeve coats the first noncoiled conductor cable and is coupled proximally to the connector and distally to the first electrode.

In accordance with still another aspect of the present invention, a lead assembly is provided. The lead assembly includes a tubular housing that has a proximal end, a fixation mechanism, and a first electrode. A lead body is provided that has a first end coupled to the proximal end of the tubular housing, a second end, and a first elongated noncoiled conductor cable that is in electrical communication with the first electrode. The lead body also includes a second electrode, a second noncoiled conductor cable in electrical communication with the second electrode, and an insulative sleeve coating the first and second noncoiled conductor cables. A connector for coupling to a cardiac stimulator is provided that has a distal end coupled to the second end of the lead body. A stylet is removably and slidably disposed within the sleeve for spatially manipulating the lead assembly.

In accordance with yet another aspect of the present invention, an electrode assembly for a cardiac lead is provided. The assembly includes a first tubular sleeve that has a proximal end, an interior surface, an exterior surface, a longitudinally extending lumen, and an opening extending from the interior surface to the exterior surface. A conductor cable is disposed in the lumen. The conductor cable has a conductor element surrounded by a second tubular sleeve. The conductor element has a distal end that is not covered by the second tubular sleeve and that projects through the opening. An electrode is disposed over the first tubular sleeve and is coupled to the distal end of the conductor element.

In accordance with still another aspect of the present invention, a method of interconnecting an individually insulated conductor cable to an electrode in a cardiac lead that has an elongated sleeve is provided. The method includes the steps of making an opening in the elongated sleeve and coupling one end of the conductor cable to the electrode. The other end of the conductor cable is fed through the opening. The electrode is slipped over the sleeve proximate the opening and the electrode is secured to the sleeve.

BRIEF DESCRIPTION OF THE DRAWINGS

The foregoing and other advantages of the invention will become apparent upon reading the following detailed description and upon reference to the drawings in which:

FIG. 1 is a pictorial view of an exemplary embodiment of a lead assembly in accordance with the present invention;

FIG. 2 is a cross-sectional view of FIG. 1 taken at section 2—2;

DETAILED DESCRIPTION OF SPECIFIC EMBODIMENTS

Figure 3:
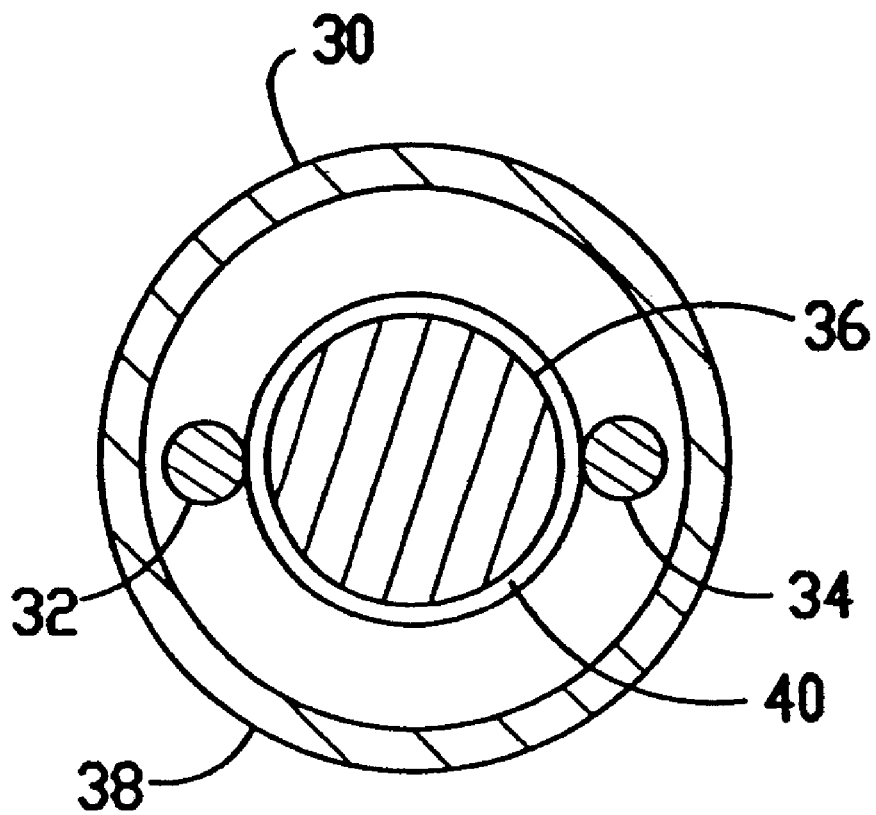
FIG. 3 is a cross-sectional view of a conventional Thinline™ lead body.

In the drawings described below, reference numerals are generally repeated where identical elements appear in more than one figure. Turning now to the drawings, and in particular to FIGS. 1 and 2, there is shown an exemplary lead assembly 10 that is adapted for either endocardial or epicardial fixation to a human heart. FIG. 1 shows a pictorial view of the lead assembly and FIG. 2 shows a cross-sectional view of FIG. 1 taken at section 2—2. The lead assembly 10 includes a lead body 12 that has a proximal end 14 provided with a connector 16 for electrical connection to a cardiac stimulator 18. The cardiac stimulator 18 may be a pacemaker, a cardioverter/defibrillator, or a sensing instrument. The proximal end 14 of the lead body 12 may be coupled to the connector 16 by conventional means such as crimping, laser, or spot welding. The distal end 20 of the lead body 12 includes an annular electrode 21 and a tubular housing 22 disposed distal to the annular electrode 21 that has another electrode 23. As discussed more below, spatial manipulation of the lead assembly 10 during implantation is accomplished by advancing a flexible stylet 24 into the lead assembly 10.

The lead body 12 consists of conductor cables 25a and 25b surrounded by a coextensive insulating sleeve 26. For a unipolar application, there may be only one conductor cable 25a or 25b, and for multipolar applications, there may be several such cables. Each conductor cable 25a and 25b consists of a conducting element 27 covered by a coextensive insulating sleeve 29. The conducting element 27 may be a single filament wire or a plurality of individual conductor wires 28 as shown. The precise number and arrangement of the conductor wires 28 is a matter of design discretion. In the embodiment shown, each conducting element 27 consists of nineteen individual metal conductor wires 28 having a combined diameter of approximately 0.127 mm. The insulating sleeves 29 have a wall thickness of approximately 0.0508 mm, making the total diameter of each conductor cable 25a or 25b approximately 0.229 mm or 0.69 French. The stylet 24 has a diameter of approximately 0.406 mm and the sleeve 26 has a wall thickness of approximately 0.152 mm. The total diameter of the lead body 12 is approximately 1.04 mm or approximately 3.12 French.

The contrast between the lead body 12 and a conventional Thinline™ lead body may be understood by referring now also to FIG. 3, which shows a cross-sectional view of a conventional Thinline™ lead body 30. The conventional lead body 30 consists of coiled and nested conductor wires 32 and 34 defining a concentrically disposed lumen 36. The conductor wires 32 and 34 are both individually insulated and surrounded by an outer insulating sleeve 38. A stylet 40 is concentrically disposed in the lumen 36. The total diameter of the lead body 30 is a combination of twice the wall thickness of the sleeve 38, the combined diameters of the conductor wires 32 and 34, and the concentrically disposed lumen 36.

In contrast to conventional lead bodies, such as the lead body 30 shown in FIG. 3, the conductor cables 25a and 25b are noncoiled, that is, not spiraled around a concentrically disposed lumen for the purpose of accommodating a concentrically disposed stylet. Instead, the noncoiled conductor cables 25a and 25b and the stylet 24 are disposed inside the sleeve 26 in a generally parallel arrangement. Consequently, the conductor cables 25a and 25b, the stylet 24, and the sleeve 26 may be manufactured with diameters that permit a dense packing of the stylet 24 and the conductor cables 25a and 25b to yield a lead body 12 with a very small total diameter. For a unipolar design, the minimum diameter of the lead body 12 is given approximately by the sum of the diameter of the stylet 24, twice the wall thickness of the sleeve 26, and the diameter of one of the cables 25a or 25b. For a multipolar design, the relationship between the diameter of the lead body 12 and the dimensions of the stylet 24 and the cables 25a and 25b is more complex.

Figure 4:
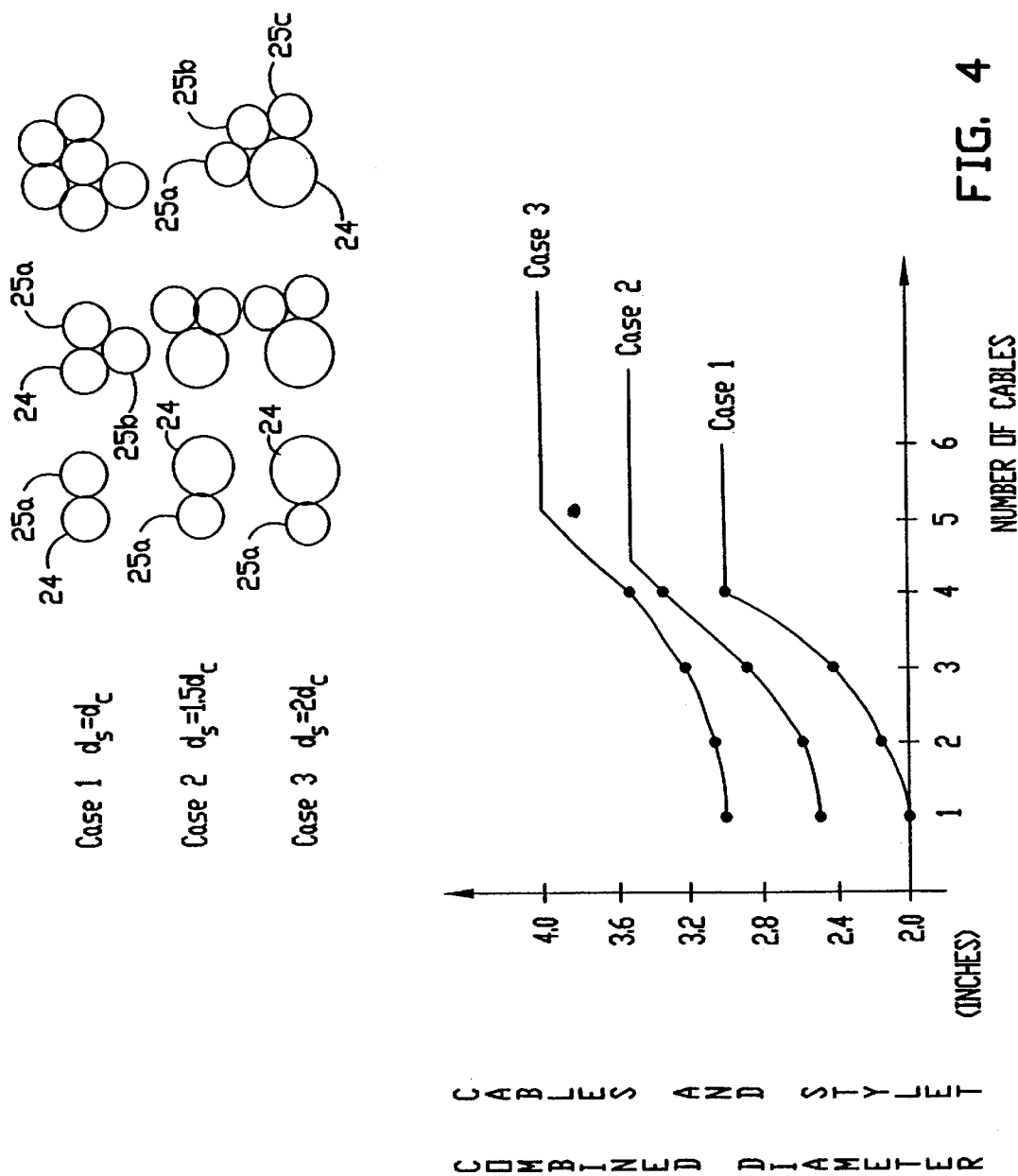
FIG. 4 is a graphical representation of the diameters of various embodiments of the lead body in accordance with the present invention.

The relationship between the diameters of the cables 25a and 25b, the stylet 24, and the overall diameter of the lead body 12, excluding the wall thickness of the sleeve 26 which may be treated as a constant, is shown empirically in a graph in FIG. 4. The x-axis of the graph is the number of conductor cables (e.g., 25a) in a given lead body. The y-axis is the total diameter of the cables 25a and 25b and the stylet 24 in inches. The variable $d_s$ represents the diameter of the stylet 24 and the variable $d_c$ represents the diameter of each of the cables 25a and 25b. All of the data points are derived by setting $d_c$ equal to 1.0 inch and determining the resulting combined diameter of the stylet 24 and the cables 25a and/or 25b graphically. The 1.0 inch figure for $d_c$ is used to simplify the graph. Obviously, the actual diameter of the cables 25a and 25b will be several orders of magnitude smaller than 1.0 inch. However, the skilled artisan will appreciate that the relationships illustrated by the graph transcend the particular units of measurement involved.

The graph illustrates three cases of different combinations of values for $d_s$ and $d_c$. The cases are set out in table form with a schematic representation of some possible combinations of stylet 24 and cables 25a and/or 25b. In the first case, Case 1, $d_s$ is equal to $d_c$. As might be expected, the curve for Case 1 shows that for a single 1.0 inch diameter cable 25a and a 1.0 inch diameter stylet 24, the x coordinate is 1, and the y coordinate, the diameter of the combination of the stylet 24 and the cable 25a, is 2.0 inches. For two cables 25a and 25b, the x coordinate is 2 and the total diameter is approximately 2.3 inches. In the third case, Case 3, $d_s$ is equal to $2d_c$. For three cables 25a, 25b, and now 25c, the x coordinate is 3 and the diameter of the combination is approximately 3.2 inches.

Figure 6:
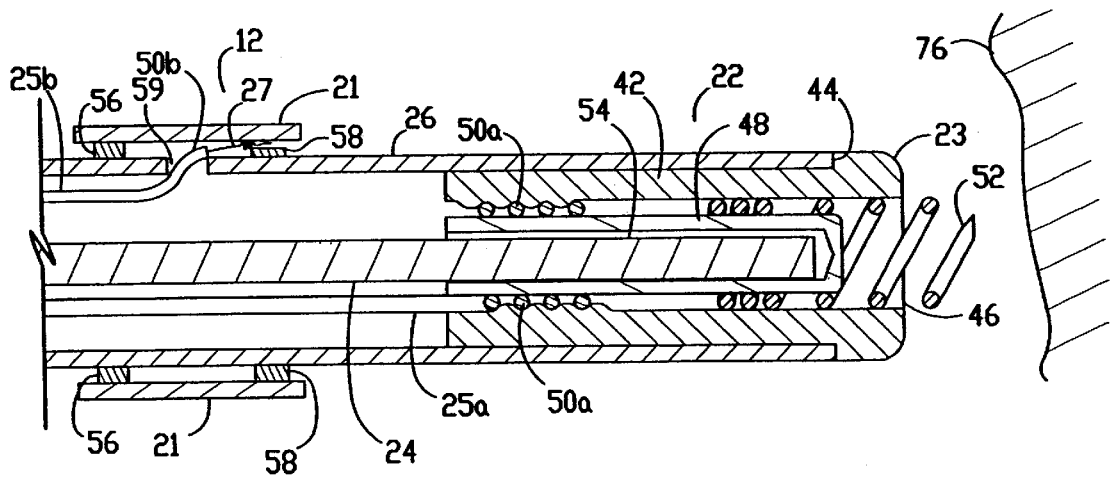
FIG. 6 is a cross-sectional view of FIG. 1 taken at section 6—6.

FIG. 6 illustrates that many different combinations of cable quantity and diameter, as well as stylet diameter may be selected to create unipolar, bipolar, or multipolar lead bodies with small diameters. The ability to densely pack the noncoiled cables with the stylet makes this flexibility in lead body design possible. Regardless of the number of cables 25a and 25b, the true minimum diameter of the lead body 12 will be slightly larger than the geometrically exact minimum so that the stylet 24 has sufficient clearance with the cables 25a and 25b and the interior of the sleeve 26 to move longitudinally without sticking.

Referring again to FIG. 2, the conductor element 27 is preferably manufactured from a biocompatible conducting material, such as, for example, MP35N alloy. MP35N alloy generally consists of a combination of cobalt, chromium, nickel, and molybdenum. A further discussion of the properties of MP35N alloy may be had by reference to U.S. Pat. Nos. 3,356,542 and 3,562,024. The lead body 12 should be capable of readily conforming to the irregular passageways and shapes of the cardiovascular system. Accordingly, the conductor element 27 should have a high enough ductility to permit the lead body 12 to flex easily, and elastically. The conductor element 27 is normally cold worked during fabrication. In the event the conductor element 27 is composed of several individual wires 28, it is anticipated that the wires 28 should be slightly twisted to keep them together prior to the application of the sleeve 29. However, the wires 28 may have a tendency to resist the twist and spring apart due to the previous cold work. In this regard, the wires 28 may be heat set so that they do not unfurl prior to the application of the sleeve 29. A variety of heat setting protocols may be suitable. One possibility involves tempering at 600° F. for approximately one hour in an inert ambient, such as argon. The fully fabricated conductor element 27 may be obtained from the Xylem Company in Wayzata, Minn.

The insulating sleeve 29 for each cable 25a and 25b is designed to provide biocompatible electrical insulation for the conductor element 27 while providing an external surface that has a low coefficient of friction relative to the stylet 24. The sleeves 29 are preferably fabricated from a biocompatible polymer material, such as, for example, ETFE (fluoropolymer resin), or a similar biocompatible polymer material.

The insulating sleeve 26 functions primarily as a flexible structure to confine the stylet 24 during implantation of the lead assembly 10. In the absence of the sleeve 26, force longitudinally applied to the stylet 24 will simply cause the stylet 24 to bend rather than advance the lead assembly 10. The sleeve 26 is advantageously fabricated from a biocompatible polymer material, such as, for example, polyurethane, polyethylene, or similar materials. If the material chosen for the sleeve 26 is rather soft and tacky, the stylet 24 may bind against the interior surface of the sleeve 26. In this regard, it is anticipated that the material used for the sleeve 26 should advantageously have a Shore hardness of about 55D or higher.

Figure 5:
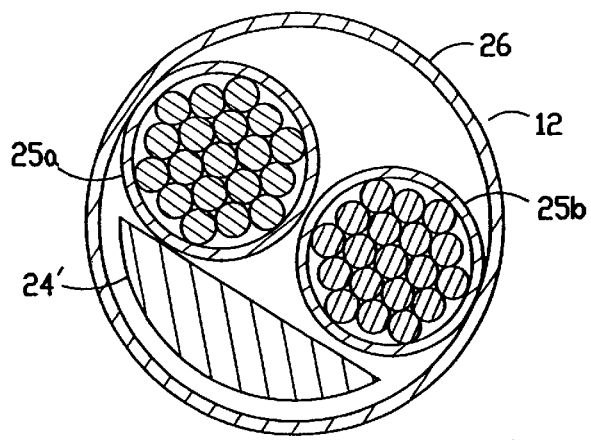
FIG. 5 is a cross-sectional view like FIG. 2 of an alternative stylet structure in accordance with the present invention.

The stylet 24 may be of conventional cylindrical design and fabricated from materials commonly used for stylets, such as, for example, stainless steel, titanium, or like materials. Alternatively, the stylet 24 may be fabricated with a hemispherical or circular segment cross-section. FIG. 5 is a cross-sectional view of the type shown in FIG. 2. The stylet, now designated 24', is provided with a circular segment cross-section. For a given size of conductor cable 25a or 25b, this non-cylindrical cross-section permits a smaller diameter sleeve 26 than is possible with the embodiment shown in FIG. 2. Regardless of the particular geometric configuration, the stylet 24 may be coated with the same materials used to fashion the sleeve 29 to reduce friction with the cables 25a and 25b as well as the interior surface of the sleeve 26.

The detailed structure of the electrode housing 22, the first or tubular electrode 23, and the second or annular electrode 21 may be understood by reference to FIGS. 1 and 6. FIG. 6 is a cross sectional view of FIG. 1 taken at section 6—6. The tubular electrode 23 of the electrode housing 22 has a proximally projecting reduced diameter portion 42 which defines a proximally projecting annular shoulder 44 located near the distal end of the tubular electrode member 23. The distal end of the sleeve 26 is secured to the exterior of the reduced diameter portion 42 and abuts against the shoulder 44. The distal end of the tubular electrode 23 includes an opening 48.

A tubular crimp slug 48 is disposed inside the tubular electrode 23. The distal end 50a of the cable 25a is looped around the proximal end of the crimp slug 48 and a fixation mechanism or corkscrew 52 is coiled around the distal end of the crimp slug 48. The distal end of the corkscrew 52 projects from the opening 46 to provide active fixation to endocardial tissue. The distal end 50a and the corkscrew 52 are secured by crimping the reduced diameter portion 42 of the tubular electrode 23 as shown. Prior to crimping, most of the insulating sleeve 29 (See FIG. 2) should be removed from the distal end 50a to expose the conductor element 27 (See FIG. 2) and to provide an electrical pathway to the electrode 23. In addition to relying on crimping to secure the distal end 50a and the corkscrew 52, spot or laser welding may be employed to provide an additional attachment mechanism in the event the slug 48 is fabricated from a weldable material. The slug 48 includes a bore 54 that extends from the proximal end of the slug 48 to the distal end of the slug 48. The bore 54 is designed to receive the stylet 24 during implantation as discussed more fully below.

Referring still to FIG. 6, the first annular electrode 21 is disposed over the sleeve 26 proximal to the electrode housing 22. Two annular members 56 and 58 are disposed between the sleeve 26 and the first annular electrode 21. To establish electrical connection between the conductor cable 25b and the annular electrode 21, the conductor cable 25b is projected through an opening 59 in the sleeve 26 located in that portion of the sleeve 26 covered by the annular electrode 21. The distal end 50b of the cable 25b is stripped off the sleeve 29 (See FIG. 2) to expose the bare conductor element 27. The bare conductor element 27 is sandwiched between the exterior of the annular member 58 and the interior of the annular electrode 21. Prior to installing the annular electrode 21, the bare conductor element 27 is secured to the annular member 58 by laser or spot welding. After the conductor element 27 is secured to the annular member 58, the annular electrode 21 is positioned and swaged. The swaging serves to reduce the diameter of the annular electrode 21 and to ensure physical contact between the annular electrode 21 and the conductor element 27 and/or the annular member 58. The annular members 56 and 58 could be eliminated and the electrode 21 secured to the sleeve 26 by interference.

Figure 7:
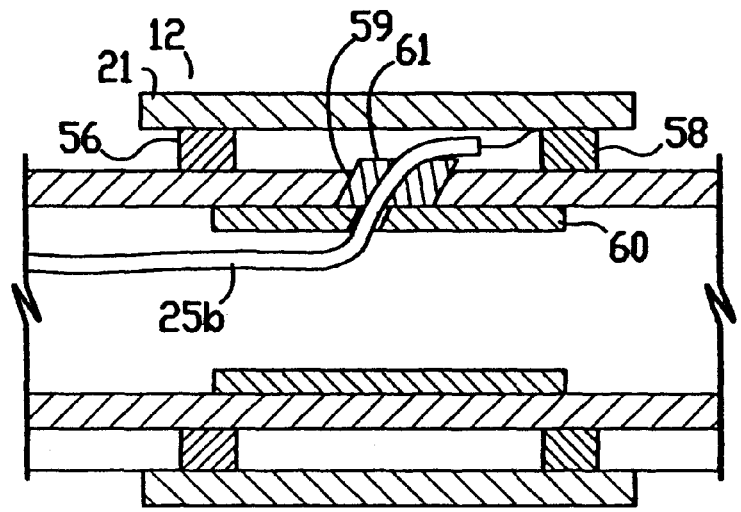
FIG. 7 is a cross-sectional view similar to FIG. 6 of an alternative cable-electrode interconnection structure in accordance with the present invention.

Depending on the tolerance of the fit between the cable 25b and the opening 59 and the flexibility of the sleeve 26, passage of body fluids through the opening 59 may be inhibited. If it is desired to provide an additional barrier to prevent the intrusion of body fluids though the opening 59, the lead body 12 may be fitted with a seal ring 60 that is disposed inside the sleeve 26 proximate the annular electrode 21 as shown in FIG. 7. The cable 25b is projected through both the seal ring 60 and the sleeve 26 and attached to the electrode 21 as described above. A pocket 61 of a biocompatible adhesive is disposed around the cable 25b to seal the opening 59 over the seal ring 60. The adhesive may be any of a variety of adhesives, such as, for example, the two-part adhesive Polycin/Vorite supplied by CasChem, Inc., or similar adhesives.

Figure 8:
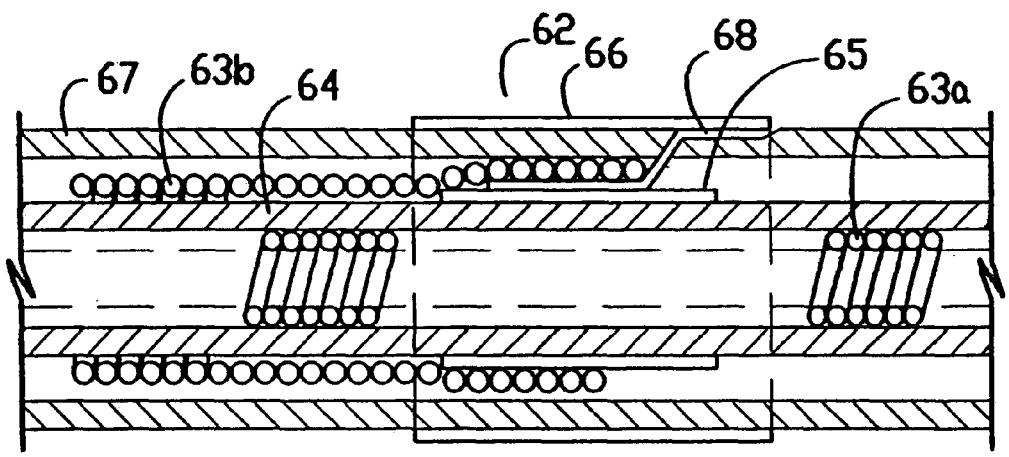
FIG. 8 is a cross-sectional view of a conventional coaxial bipolar lead.

The interconnection structures shown in FIGS. 6 and 7 may be used to connect an individually insulated coiled cable, such as the Thinline™, as well as the aforementioned noncoiled cable 25b, to the electrode 21. Regardless of the type of cable involved, the interconnection structure depicted in FIGS. 6 and 7 exhibits advantages over the conventional structure for coupling separately insulated lead cables to a proximally disposed annular electrode in a conventional coaxial bipolar lead. The conventional lead and interconnection structure are shown in FIG. 8. The lead 62 includes an inner coiled cable 63a and an outer coiled cable 63b separated by an inner insulating sleeve 64. An inner ring 65 is disposed around the inner sleeve 64 proximate an electrode 66. An outer sleeve 67 surrounds the outer coiled cable 63b. To establish connection between the outer cable 63b and the electrode 66, a metallic connection tab 68 is provided that projects through the outer sleeve 67 and is connected at one end to the electrode 66 and is disposed at the other end between the ring 65 and the outer coiled cable 63b. Assembly of the interconnection structure shown in FIG. 8 is time consuming and costly. The interconnection structures shown in FIGS. 6 and 7 eliminate the connection tab 68 and the inner sleeve 64, yielding a structure that is simpler and easier to assemble.

Figure 9:
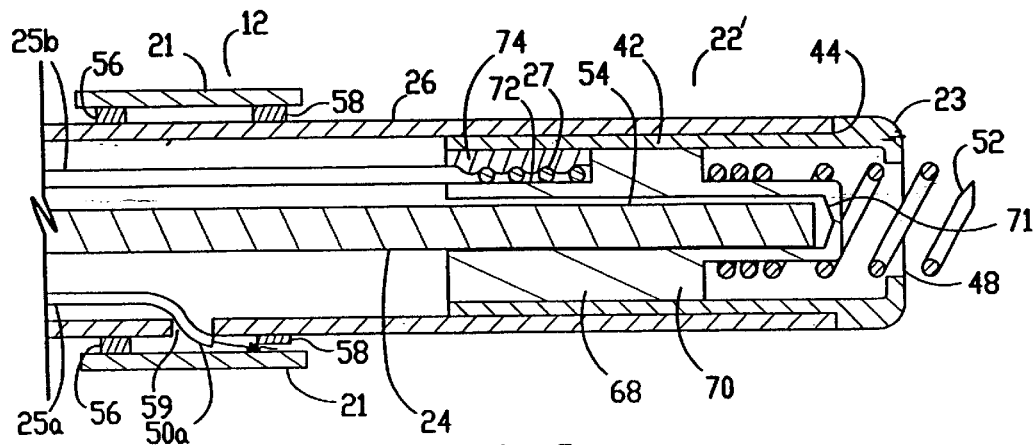
FIG. 9 is a cross-sectional view like FIG. 6 of an alternate embodiment of the electrode housing in accordance with the present invention.

A myriad of structures may be used to secure one of the cables 25a or 25b to the electrode housing 22. FIG. 9 is a view of similar perspective to FIG. 6 and shows a cross-sectional view of one such example of an alternative structure. In this embodiment, attachment of the conductor cable 25a to the annular electrode 21 may be accomplished by the method and structure described above with regard to FIG. 6.

To secure the other cable 25b, a different structure is provided. A semi-tubular plug 69 is disposed inside the tubular electrode 23. The central portion 70 of the plug 69 includes a cylindrical surface that is sized to provide an interference fit with the interior surface of the tubular electrode 23. The distal portion of the plug 69 includes a reduced diameter cylindrical tip 71. The fixation mechanism or corkscrew 52 is coiled around the exterior of the tip 71. The distal end of the corkscrew 52 projects from the opening 46 to provide active fixation to endocardial tissue. The plug 69 includes the bore 54 disclosed above.

Figure 10:
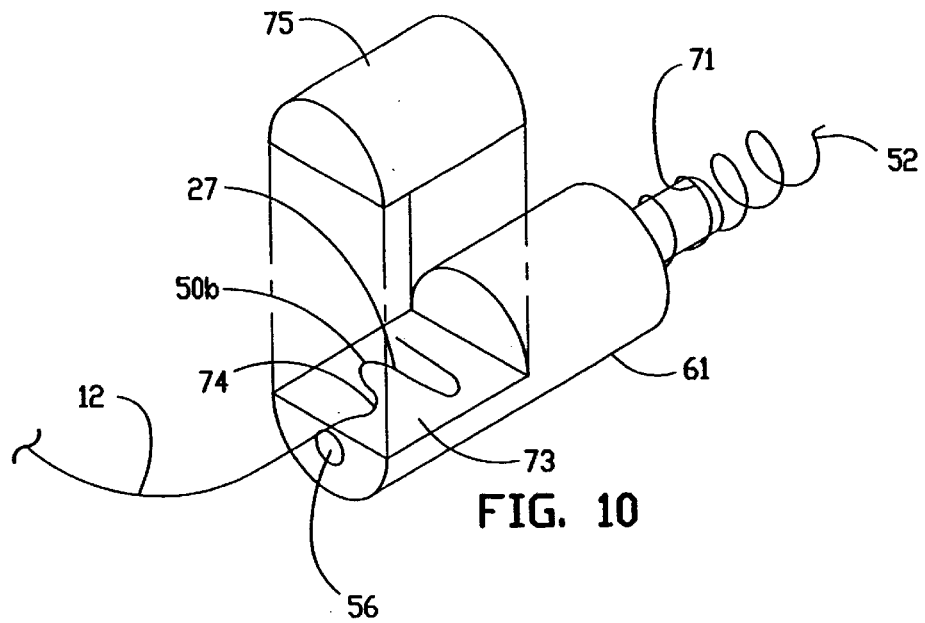
FIG. 10 is an exploded pictorial view of a portion of the electrode housing depicted in FIG. 9 in accordance with the present invention.

The upper side of the proximal portion of the plug 69, as viewed in FIG. 9, includes a cut-out 72, the structure and function of which may be understood by referring now also to FIG. 10, which is an exploded pictorial view of the plug 69 removed from the electrode housing, now designated 22'. The horizontal surface 73 of the cut-out 72 provides a platform upon which the distal end 50b of the conductor cable 25b may be secured. The distal end 50b is disposed on the horizontal surface 73 in a serpentine-like fashion. Most of the insulating sleeve 29 (See FIG. 2) should be removed from the distal end 50b to expose the conductor element 27. The particular configuration of the serpentine-like arrangement is a matter of discretion. However, care should be taken to provide the first bend 74 in the distal end 50b with a relatively large radius to reduce the potential for a stress riser.

A crimp block 75 is provided to secure the distal end 50b of the cable 25b to the plug 69. The crimp block 75 is dimensioned to correspond to the cut-out 68, and when pressed tightly on the cut-out 68 and over the distal end 50b, acts as a crimping member to hold the distal end 50b in place as shown in FIG. 10. The crimp block 75 is dimensioned to provide an interference fit with the interior surface of the reduced diameter portion 42 of the tubular electrode 23. In addition to relying on friction to secure the cable 25b to the electrode housing 22, the conductor element 27 may also be spot or laser welded to the horizontal surface 70 to provide an additional attachment mechanism in the event the plug 69 is fabricated from a weldable material.

For a unipolar configuration of the lead assembly 10, one or the other of the electrodes 21 and 23 may be eliminated or simply not connected to the single conductor cable 25a or 25b. To create a multipolar lead assembly 10, a plurality of cables and electrodes of the types described above may be incorporated.

Figure 11:
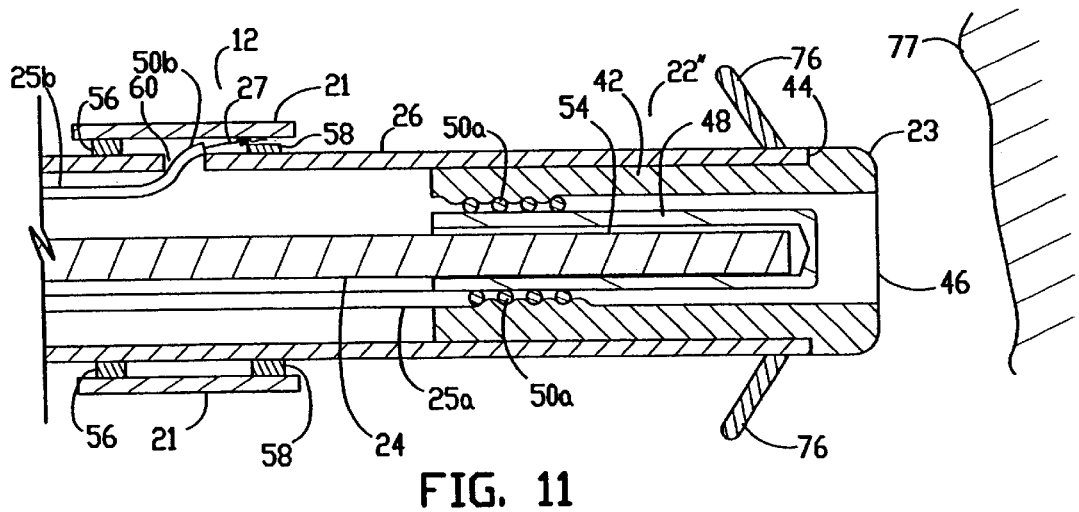
FIG. 11 is a cross-sectional view like FIG. 6 of an alternate embodiment of the electrode housing in accordance with the present invention.

The fixation mechanism or corkscrew 52 may be replaced by a passive fixation mechanism to secure the electrode housing 22 to endocardial tissue. FIG. 11 is a view of similar perspective to FIG. 9 and shows an embodiment of the electrode housing, now designated 22", that includes one or more outwardly projecting tines 76 that provide passive fixation. The number and arrangement of the tines 76 is a matter of design discretion. The tines 76 may be composed of a non-metallic biocompatible material, such as, for example, silicone rubber, polyurethane, polyethylene, polyimide, or similar materials.

The corkscrew 52, the electrodes 21 and 23, and the annular members 58 and 60 may be fabricated from a variety of biocompatible conducting materials, such as, for example, iridium oxide coated titanium. Other possible materials include MP35N, stainless steel, platinum-iridium alloy consisting of approximately 90% platinum and 10% iridium, or some other biocompatible conducting metal. The corkscrew 52 is preferably coated with a thin coating of an insulating polymer, such as Parylene C® supplied by Union Carbide, or a similar material. In general, the plug 69 and crimp block 75 may be fabricated from the same types of materials as the corkscrew 52, or may be composed of a non-metallic, biocompatible material, such as, for example, polyurethane, polyethylene, polyimide, or similar materials. If the plug 69 is composed of a metallic material, the corkscrew 52 may be secured to the tip 64 by spot or laser welding. However, an electrical pathway must be established between the distal end 50b of the cable 25b and the tubular electrode 23. If the plug 69 is fabricated from a metallic material, this pathway is provided by the plug 69 itself. In this circumstance, the crimp block 75 need not be composed of a conducting material and may instead be fabricated from a variety of biocompatible, nonconducting materials, such as polyurethane, polyethylene, polyimide, or similar materials. However, if the plug 69 is fabricated from a nonconducting material, the crimp block 75 should be fabricated from the same types of materials as the corkscrew 52 to establish the requisite electrical pathway from the conductor element 27 to the tubular electrode 23.

The implantation procedure of the lead assembly 10 may be understood by reference to FIGS. 1 and 6. The stylet 24 is introduced into the lead body 12 and advanced longitudinally to the position shown in FIG. 6. The electrode housing 22 is introduced into one of the major veins leading to the heart, such as the subclavian vein or one of the internal jugular veins. Following initial transvenous entry, the electrode housing 22 is advanced by manipulation of the stylet 24 until the electrode housing 22 is located at the desired point of fixation to the endocardium 77. If active fixation is employed, the surgeon may then twist the lead body 12 or the connector 16 to engage the cork screw 52 with the endocardium 77. If not, the surgeon need not twist the lead body 12. The stylet 24 may then be retracted and the connector 16 connected to the cardiac stimulator 18. If the initial placement is unsatisfactory, the procedure may be reversed and repeated as often as necessary.

Figure 12:
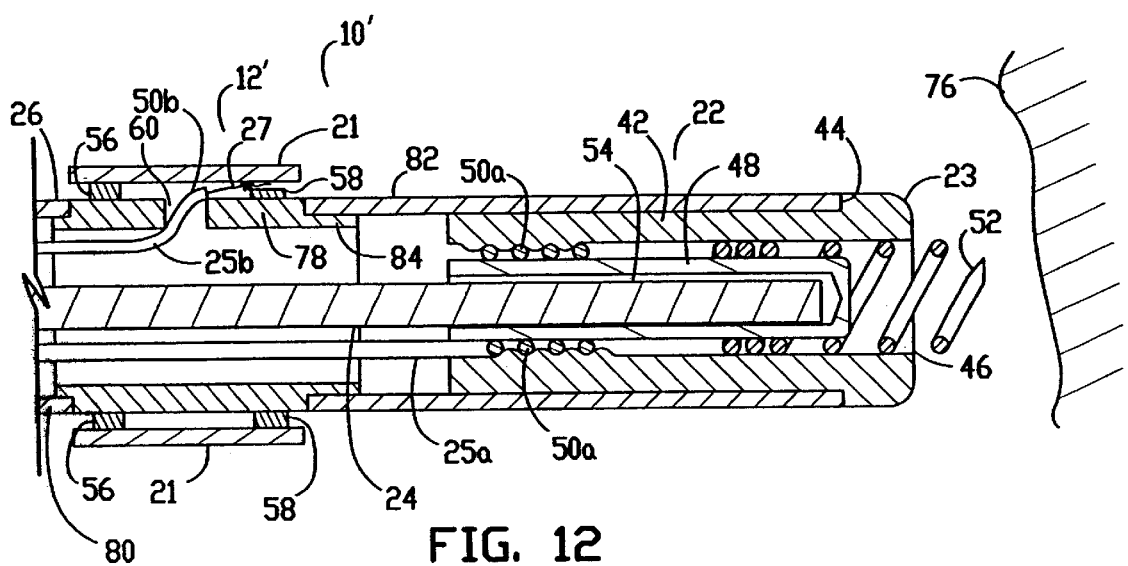
FIG. 12 is a cross-sectional view like FIG. 6 of an alternate embodiment of the lead assembly incorporating a dissolvable sleeve in accordance with the present invention.

As noted above, the sleeve 26 serves to confine the bending of the stylet 24 during implantation of the lead assembly 10. This requirement is transitory since the stylet 24 is removed after the lead assembly 10 is implanted. It follows then that the sleeve 26 can be eliminated after implantation, resulting in a significant reduction in the overall diameter of the structure disposed in the patient's cardiovascular system. FIG. 12 is a cross-sectional view from the same perspective as FIG. 6, and shows an alternate embodiment of the lead assembly, now designated 10', that incorporates a dissolvable sleeve, now designated 26'. Structure is provided to secure the electrode 21 to the electrode housing 22 since the sleeve 26' will dissolve after implantation. In this regard, an annular fitting 78 is provided. The electrode 21 and the annular members 56 and 58 are swaged around the annular fitting 78 and the cable 25b is connected to the electrode 21 in the same fashion as described above. The annular fitting 78 is provided with a reduced diameter proximal portion 80 over which the sleeve 26' is disposed. Physical connection between the annular fitting 78 and the electrode housing 22 is made via another sleeve 82 that is disposed proximally over a reduced diameter distal portion 84 of the annular fitting 78 and is coupled distally to the electrode housing 22 in the same fashion as the sleeve 26 described in FIG. 6 above. The sleeve 82 may be fabricated from the same materials as the sleeve 26 described in FIG. 6 above.

The procedure for implantation of the lead assembly 10' will be the same as disclosed above. However, the sleeve 26' will dissolve after some weeks in the body. A variety of biocompatible body absorbable materials may be used to fabricate the sleeve 26', such as, for example polylactic acid polyglycolic acid, polyvinyl alcohol, or similar materials. It is anticipated that the sleeve 26' constructed of such materials will dissolve after a few weeks, leaving only the cables 25a and 25b disposed in the patient's cardiovascular system between the connector (See FIG. 1) and the annular fitting 78. The annular fitting 78 may be fabricated from the same types of materials used to make the plug 69 described in FIG. 9 above.

Figure 13:
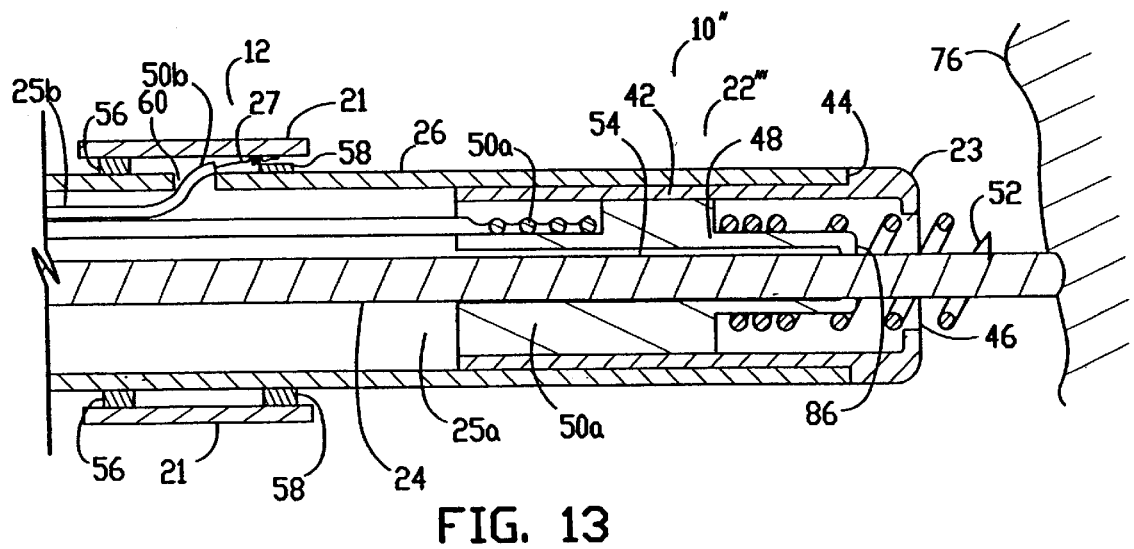
FIG. 13 is a cross-sectional view like FIG. 6 showing an alternate embodiment of the electrode housing configured to slide over a stylet in accordance with the present invention.

FIG. 13 is a partial sectional view of an alternate embodiment of the lead assembly, now designated 10", taken at the same general section as FIG. 6. In this embodiment, a particular pathway to the desired fixation point on the endocardium 77 is preestablished using the stylet 24. In this regard, the stylet 24 is initially implanted transvenously to the desired location proximate the endocardium 77. The distal end of the plug 48 is provided with an opening 86 so that the electrode housing, now designated 22''', may then be slipped over the proximal end of the stylet 24 and advanced along the stylet 24 to the preestablished site of endocardial fixation. The corkscrew 52 may then be secured to the endocardium 77 as disclosed above, either with the stylet 24 still in place or after the stylet 24 has been withdrawn. After the corkscrew 52 has been secured to the endocardium 77, the stylet 24, if still in place, may be removed.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method comprising:
   making an opening in an elongate sleeve of a cardiac lead;
   coupling one end of a non-coiled conductor cable to an electrode of the cardiac lead;
   feeding a second end of the conductor cable through the opening;
   slipping the electrode over the sleeve over the opening;
   securing the electrode to the sleeve; and
   positioning a stylet within the elongate sleeve parallel and offset to the conductor cable.

2. The method as recited in claim 1, comprising:
   providing an annular member between the sleeve and the electrode;
   coupling the non-coiled cable to the annular member; and
   swaging the electrode.

3. The method as recited in claim 1, further comprising positioning a seal ring inside the sleeve proximate to the electrode, making a passage in the seal ring, feeding the other end of the conductor cable through the passage, and applying an adhesive in the opening to secure the second end of the conductor cable.

4. The method as recited in claim 1, wherein making the opening in the elongate sleeve includes making an opening in a sleeve composed of a body dissolvable material.

5. The method as recited in claim 4, wherein the body dissolvable material has a Shore hardness of about 55D or higher.

6. The method as recited in claim 1, further comprising reducing a diameter of the electrode.

7. A method comprising:
   disposing at least one conductor cable within an elongate sleeve of a body dissolvable material;
   making an opening in the elongate sleeve;
   coupling a first end of the cable to an electrode of a cardiac lead;
   providing a second end of the conductor cable through the opening;
   slipping the electrode over the sleeve proximate to the opening; and
   securing the electrode to the sleeve.

8. The method as recited in claim 7, further comprising:
   positioning a seal ring inside the sleeve proximate the electrode;
   making a passage in the seal ring; and
   feeding the second end of the conductor cable through the passage.

9. The method as recited in claim 8, further comprising applying an adhesive in the opening and securing the second end of the conductor cable.

10. The method as recited in claim 7, wherein securing the electrode includes swaging an annular electrode to a second annular member.

11. The method as recited in claim 7, wherein the portion of lead is an annular fitting having an opening and having at least one annular member, and further including coupling a first portion of a biocompatible sleeve to a first electrode, coupling a second portion of a biocompatible sleeve to the annular fitting, the annular fitting being supported relative to the first electrode by the biocompatible sleeve.

12. The method as recited in claim 11, further comprising coupling a sleeve composed of a body dissolvable material to the annular fitting.

13. The method as recited in claim 12, wherein coupling the sleeve of body dissolvable material includes coupling a sleeve having a Shore hardness of about 55D or higher.

14. The method as recited in claim 12, wherein the body dissolvable material is selected from the group consisting of polylactic acid, polyglycolic acid, and polyvinyl alcohol.

15. A method comprising:
   disposing at least one conductor cable within an elongate sleeve of a body dissolvable material;
   making an opening in the elongate sleeve;
   coupling a first end of the cable to an electrode of a cardiac lead;
   providing a second end of the conductor cable through the opening;
   slipping the electrode over the sleeve proximate to the opening;
   securing the electrode to the sleeve;
   disposing a stylet within the elongate sleeve; and
   removing the sleeve from the conductor cable.

16. The method as recited in claim 15, wherein removing the sleeve from the conductor cable includes dissolving the sleeve from the conductor cable.

17. The method as recited in claim 15, further comprising removing the stylet prior to removing the sleeve from the conductor cable.

18. The method as recited in claim 15, wherein disposing the stylet within the elongate sleeve includes disposing a stylet having a non-cylindrical cross-section within the sleeve.

19. The method as recited in claim 15, wherein disposing the stylet within the elongate sleeve includes disposing a stylet offset to a longitudinal axis of the sleeve, and non-concentrical relative to the sleeve.

* * * * *